US006428753B2

(12) United States Patent
Freeman

(10) Patent No.: US 6,428,753 B2
(45) Date of Patent: *Aug. 6, 2002

(54) DECORATIVE CANDLE AND METHOD OF MANUFACTURING THE SAME

(76) Inventor: Faith Freeman, 3632 Rebel Cir., Huntington Beach, CA (US) 92649

( * ) Notice: Subject to any disclaimer, the term of this patent is extended or adjusted under 35 U.S.C. 154(b) by 0 days.

This patent is subject to a terminal disclaimer.

(21) Appl. No.: 09/795,751

(22) Filed: Feb. 28, 2001

Related U.S. Application Data

(63) Continuation of application No. 09/245,098, filed on Feb. 8, 1999, now Pat. No. 6,214,295.

(51) Int. Cl.[7] .......................... A61L 9/012; F23D 3/16

(52) U.S. Cl. ......................... 422/126; 44/600; 431/288; D26/6

(58) Field of Search ....................... 422/5, 126; 44/275, 44/530, 600; 431/288; D26/6

(56) References Cited

U.S. PATENT DOCUMENTS 3,797,990 A * 3/1974 Rogers et al. .............. 431/291
4,568,270 A * 2/1986 Marcus et al. .............. 431/288
4,917,597 A * 4/1990 Henze ........................ 431/298
5,338,187 A * 8/1994 Elharar ....................... 431/288
6,068,472 A * 5/2000 Freeman et al. ............ 431/291
6,079,975 A * 6/2000 Conover ..................... 431/288
6,096,102 A * 8/2000 Matthai et al. ............... 44/275
6,129,771 A * 10/2000 Ficke et al. .................... 44/275
6,214,295 B1 * 4/2001 Freeman ..................... 422/126

OTHER PUBLICATIONS

"What Is Wax?—Petroleum Wax Manufacturing—Simple Overview"; 2 pages, Prior Art.
"Candle Making—Waxes"; 3 pages, Prior Art.
"Making Candles" By Mary Talbot; 3 pages, Prior Art.
"Candle Creations" by James W. Gick, Jr.; 3 pages, Prior Art.
"Homespun Floral Candles"; Country Living Gardener; Nov./Dec. 1996; pp. 92 and 93.

* cited by examiner

*Primary Examiner*—Elizabeth McKane
(74) *Attorney, Agent, or Firm*—Stetina Brunda Garred & Brucker

(57) ABSTRACT

A method of forming a decorative candle. The method comprises providing a candle which is fabricated from a wax material that defines a top surface. Next, a source of heat is applied to the candle until at least that portion of the wax which defines the top surface thereof is melted. Then at least one gelatinous component formed from a mineral oil gel is placed onto the top surface such that the component is at least partially inserted into the molten wax. The candle is allowed to cool thereby hardening the molten wax and securing the gelatinous component. The melting point of the gelatinous component is higher than the melting point of the wax such that the component will not melt when placed upon the molten wax.

28 Claims, 2 Drawing Sheets

DECORATIVE CANDLE AND METHOD OF MANUFACTURING THE SAME

CROSS REFERENCE TO RELATED APPLICATIONS

This application is a continuation of U.S. patent application Ser. No. 09/245,098, filed Feb. 8, 1999 now U.S. Pat. No. 6,214,295.

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention generally relates to decorative candles and more particularly to a decorative candle including uniquely shaped, integral gel components.

Candles have become popular for decorative purposes and as such are being formed in different styles, shapes, and colors. Additionally, scented candles are gaining popularity for their perceived therapeutic value in aromatherapy. Typically, there are three different types of candles: tapered, molded and container. The candles may be manufactured from a wax such as paraffin, vegetable, or beeswax.

A container candle is formed by pouring melted wax into a container having a wick disposed therein. The wick is extensible through the wax such that as the wick is burned, the wax around the wick will melt thereby providing fuel for the wick to burn. A molded candle is formed by pouring melted wax into a mold containing a wick. The wax is allowed to cool such that it solidifies and is then removable from the mold thereby forming the candle. Tapered candles are formed by dipping a wick into melted wax. Each time the candle is dipped into the melted wax, the wax adheres to itself thereby forming the tapered candle.

Different types of paraffin waxes may be used for different types of candles. For instance, candles made in a container may be formed from container wax. This wax has a relatively high oil content and a relatively low melting point of between about 125° F. and 138° F. or lower. The relatively high oil content of this type of wax allows for a long burning candle. Mold wax which has a melting point between 139° F. and 143° F. is used for molded candles because the wax does not contain much oil and therefore can retain its form after removal from the mold. Tapered candles are formed from dipping wax which typically has a melting point of around 145° F. The high melting temperature allows the wax to adhere to itself as it is being dipped thereby forming a tapered candle.

Additionally, fragrances and/or pigments can be added to the wax to give the candle a unique appearance. Typically, the fragrance and/or pigment is mixed with the wax when in a melted state. The wax containing the fragrance or pigment is then formed into the preferred type of candle. The pigment will give the candle a desired coloring while the fragrance gives the candle a preferred scent. The scent produced by the fragrance may become more pronounced as the candle and therefore the fragrance are being burned.

In addition to making candles out of wax, mineral oil has been used to make candles (e.g., gel candles). The mineral oil is gelatinous at room temperature such that it can retain its form unsupported. Typically, a gel candle is formed by pouring melted mineral oil into a container having a wick. The mineral oil is allowed to cool to its gelatinous state thereby forming a candle within the container. Gel candles burn longer than candles made from paraffin wax because of the high oil content of the gel. As with traditional paraffin wax candles, gel candles may additionally be scented and/or colored to add more variety.

The present invention comprises a candle fabricated from paraffin wax and gelatinous mineral oil components. The components are used as a decorative element that additionally allow the candle to burn longer. Therefore, the candle of the present invention has a distinctive decorative style and burns longer than traditional wax candles.

BRIEF SUMMARY OF THE INVENTION

In accordance with the preferred embodiment of the present invention, there is provided a method of manufacturing a decorative candle comprising the step of providing a candle fabricated from a wax material (e.g., paraffin wax) which defines a top surface. Next, a source of heat is applied to the candle until the portion defining the top surface is melted. Then, at least one gelatinous component is placed onto the top surface such that the component is at least partially inserted into the molten wax. The candle is then cooled to harden the molten wax and secure the component to the candle.

The candle may be fabricated by first providing a container and placing a wick therein. Next, a quantity of wax is melted and poured into the container. The wax is allowed to cool until it hardens into the candle. A fragrance and/or a pigment may be added to the wax while it is in a molten state in order to give the wax a desired color and pigment.

The gelatinous component may be fabricated by melting a quantity of a mineral oil gel and then forming the molten gel into a generally planar sheet. The sheet is then cooled and cut with a die to form the component. Alternatively, the component may be fabricated by extruding and cooling the molten mineral oil gel through a die to form an extruded member. The extruded member is then cut to form the at least one gelatinous component. While the gel is molten, a fragrance and/or a pigment may be added to the gel to produce a desired color and/or scent.

Therefore, the above mentioned steps produce a decorative candle comprising a container having an open end and a quantity of wax disposed therein. The wax has a top surface that is adjacent to the open end of the container. The candle additionally comprises a wick disposed within the wax and protruding upwardly from the top surface, and at least one gelatinous component partially disposed within the top surface of the wax. Typically, the wax will be a paraffin based wax and the gelatinous component will be formed from mineral oil gel. Both the wax and the component may comprise a pigment and/or a fragrance.

BRIEF DESCRIPTION OF THE DRAWINGS

These as well as other features of the present invention, will become more apparent upon reference to the drawings wherein.

DETAILED DESCRIPTION OF THE INVENTION

Figure 1:
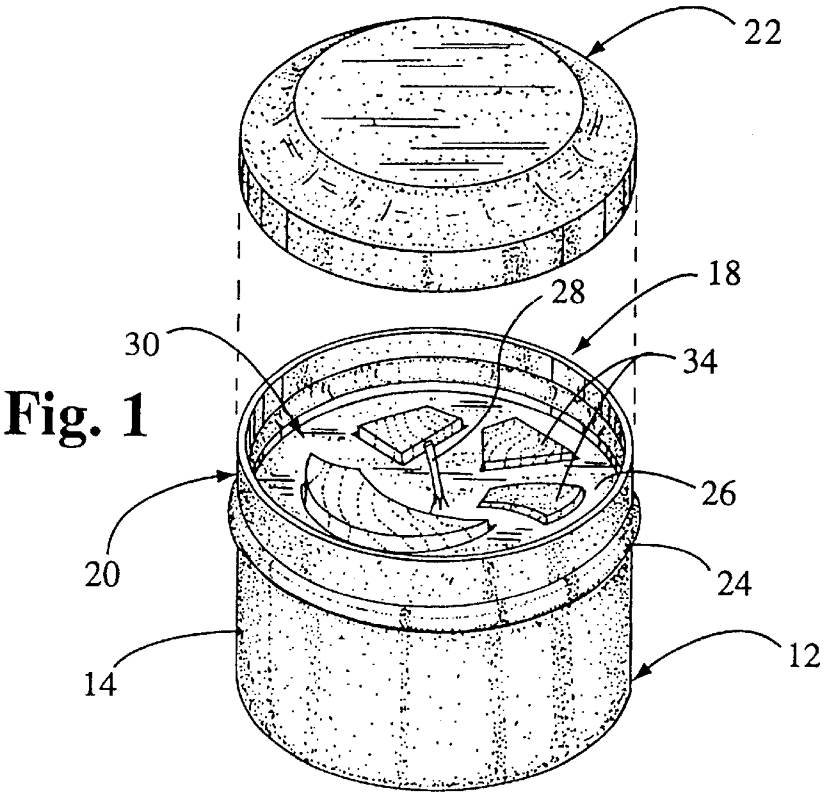
FIG. 1 is a top perspective view of the decorative candle fabricated in accordance with the preferred embodiment of the present invention.
Figure 4:
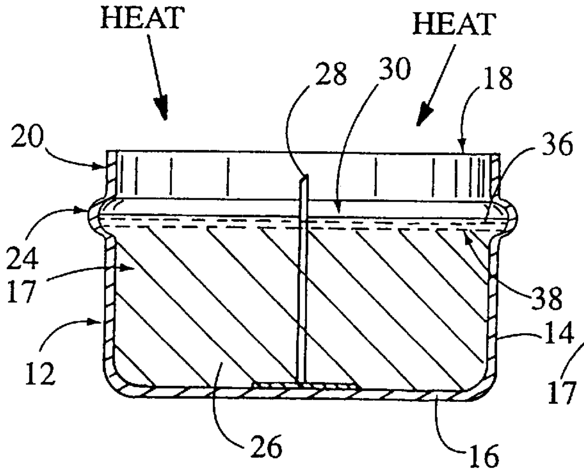
FIG. 4 is a cross-sectional view showing the wax portion of the candle shown in FIG. 1 formed in accordance with the steps shown in FIG. 2.
Figure 5:
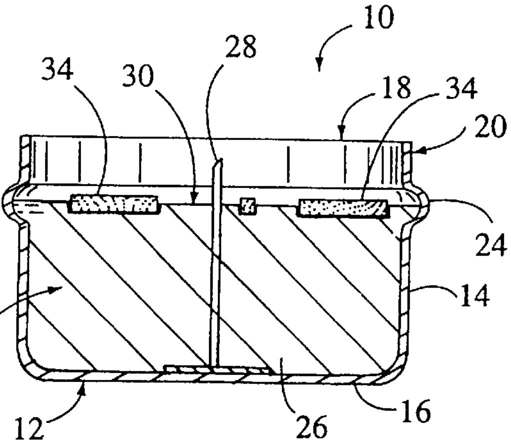
FIG. 5 is a cross-sectional view of the candle shown in FIG. 1.

Referring now to the drawings wherein the showings are for purposes of illustrating a preferred embodiment of the present invention only, and not for purposes of limiting the same, FIG. 1 is a perspective view of a wax and gel candle 10 manufactured in accordance with the preferred method of the present invention. The candle 10 comprises a container 12 formed from a metallic material. As seen in FIGS. 1, 4 and 5, the container 12 is generally cylindrical such that it comprises a side wall 14 having a generally circular configuration that extends perpendicularly from a circular bottom wall 16. The side wall 14 and the bottom wall 16 define an enclosable interior compartment 17 and an open end 18 formed about a top portion 20. The container 12 additionally comprises a lid 22 with a generally circular cross-sectional configuration used to extinguish the candle 10. The diameter of lid 22 is sized slightly larger than the diameter of the circularly configured side wall 14. Therefore, as seen in FIG. 1, the lid is placeable over open end 18 of container 12 to extinguish any flame of candle 10. The container 12 is provided with a lip 24 disposed about the exterior surface of the side wall 14. The lip 24 is placed about the top portion 20 of container 12 such that lid 22 makes abutting contact with lip 24 when placed over open end 18.

Disposed within the candle 12 is a prescribed volume of wax 26 and a wick 28 typically made from woven cotton or linen thread. It is contemplated that the wax 26 is a food grade paraffin wax with a melting point of between about 125° F. to about 145° F. The wax may be mixed with a FD&C ornamental pigment or dye to make the wax a desired color. Additionally, a fragrance such as an oil may be mixed with the wax to provide an aroma or scent as the candle 10 is burned. As seen FIG. 5, the wick 28 protrudes upwardly from an upper surface 30 of wax 26. The upper surface of wax 26 is formed such that it extends in generally parallel relation to bottom 16. Additionally, the wick 28 is positioned within wax 26 such that it extends from bottom 16 to the approximate center of top surface 30.

Placed into the wax 26 at top surface 30 are a plurality of gelatinous components 34. The components 34 are formed from a gelatinous mineral oil that has a melting point higher than the wax 26 and is used in the manufacturing of conventional gel candles. The mineral oil gel is solid, yet flexible and capable of retaining its shape unsupported at ambient temperature. Additionally, pigments and/or fragrances may be mixed with the gel in order to provide a desired color and/or scent. Examples of such mineral oil gels are "Candle Gel" and "Versa Gel" both of which are manufactured by Penrico of Woodlands, Tex.

As seen in FIG. 1, the gelatinous components 34 can be configured into decorative designs and shapes that adorn the top surface 30 of wax 26. The components 34 are affixed into the wax 26 about ⅛" below the top surface 30 by a method that will be further explained below. For decorative purposes, it is preferable that the gelatinous components 34 have a height that is greater than the depth they are inserted into the wax 26 such that a portion of each component 34 protrudes above top surface 30. The heat produced by a flame burning wick 28 of candle 10 melts the wax 26 and the gelatinous components 34. The components 34 provide mineral oil which is used by the flame on wick 28 as an additional fuel rather than just wax 26. Therefore, the wick 28 will not only burn candle wax 26, but also the mineral oil from gelatinous components 34, thereby prolonging the life of candle 10.

Figure 2:
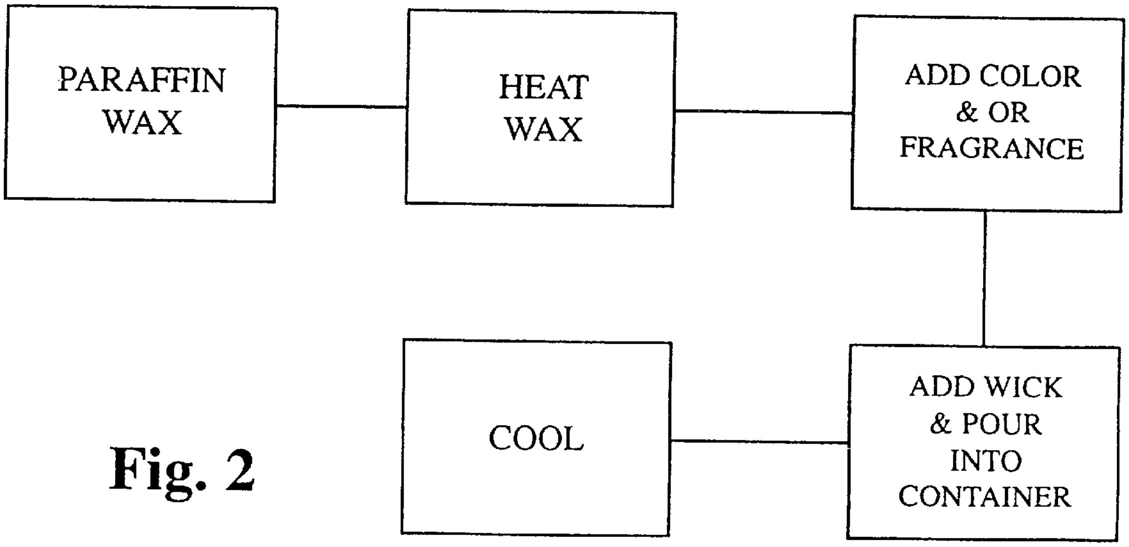
FIG. 2 is a block diagram showing the steps involved in forming the wax portion of the candle shown in FIG. 1.

With reference to FIG. 2, the preferred method of manufacturing the decorative candle 10 is to first provide a prescribed quantity of food grade paraffin wax 26 that will be used in container 12 of candle 10. Next, the wax 26 is heated via an induction or flame method to a temperature at which the wax 26 melts into a liquid solution (i.e., about 125° F. to about 145° F.). At this point, while the wax 26 is molten, the desired fragrance and/or pigment may be mixed with the wax 26. The wick 28 is placed within container 12 and positioned as previously described above. The wax 26 is then poured through the open end 18 of container 12 into interior compartment 17 and then allowed to cool until it solidifies.

Figure 3:
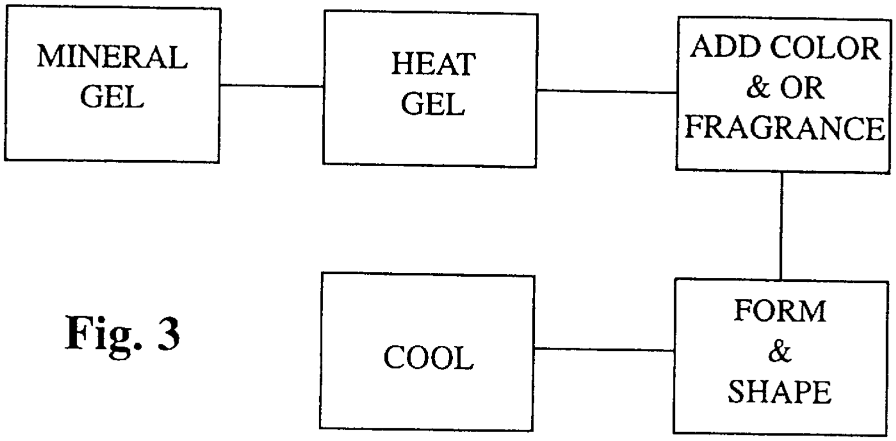
FIG. 3 is a block diagram showing the steps involved in forming the gel portion of the candle shown in FIG. 1.

With reference to FIG. 3, the gelatinous components 34 are formed by providing a prescribed quantity of the mineral oil gel previously described above. The mineral oil gel is heated via an induction or flame method until the gel melts into a liquid. Then a desired color and/or fragrance may be mixed with the gel. The gelatinous components 34 can be made by forming the gel into a planar sheet of material with a desired thickness. Next, the sheet of material is cooled and components 34 are cut from the sheet with a die. Alternatively, the components 34 may be formed by extruding the heated gel through a die, allowing the extruded member to cool and then cutting the extruded member into components 34 of a desired thickness.

In order to affix the components 34 into the wax 26, the top surface 30 is heated to the wax melting point. The top surface 30 is heated typically through an induction or infrared method whereby heat may only be applied to the top portion 20 of container 12. Therefore, the wax 26 is melted only to a depth that the gelatinous components 34 are to placed into the wax 26. As seen in FIG. 4, the wax 26 will melt forming a molten portion 36 with a solid surface 38. The components 34 are placed into the molten portion 36 of wax 26 at a desired location and supported by the solid surface 38. The components 34 are supported by the solid surface 38 such that the molten portion 36 surrounds a lower portion of each shape 34 as seen in FIG. 5. The melting point of the wax 26 is lower than the melting point of the gelatinous components 34 such that the components 34 do not melt when placed within molten portion 36. After the components 34 are positioned, the wax 26 is allowed to cool thereby solidifying around each component 34 as seen in FIGS. 1 and 5. The solidified wax 26 around each component 34 thereby secures each shape 34 thereinto.

Additional modifications and improvements of the present invention may also be apparent to those of ordinary skill in the art such as varying the configuration of container 12 and/or the shape of components 34. Thus, the particular combination of parts described and illustrated herein is intended to represent only certain embodiments of the present invention, and is not intended to serve as limitations of alternative devices within the spirit and scope of the invention.

What is claimed is:

1. A method of manufacturing a decorative candle comprising the steps of:

a) providing a candle which is fabricated from a wax material and defines a melted top surface;

b) placing at least one gelatinous component onto the melted top surface such that the component is at least partially inserted into the molten wax; and c) cooling the candle to harden the molten wax and secure the component to the candle.

2. The method of claim 1 wherein step (a) comprises providing a candle which is fabricated from a paraffin wax material.

3. The method of claim 1 wherein step (a) comprises:

i) providing a container;

ii) placing a wick within the container;

iii) melting a quantity of wax; and iv) pouring the molten wax into the container.

4. The method of claim 3 wherein step (a) (iii) further comprises adding a fragrance to the molten wax.

5. The method of claim 3 wherein step (a) (iii) further comprises adding a pigment to the molten wax.

6. The method of claim 5 wherein step (a) (iii) further comprises adding a fragrance to the molten wax.

7. The method of claim 6 wherein step (b) comprises:

i) providing a quantity of mineral oil gel;

ii) melting the mineral oil gel;

iii) forming the molten mineral oil gel into a generally planar sheet;

iv) cooling the mineral oil gel until the sheet solidifies; and v) cutting the sheet with die to form the component.

8. The method of claim 7 wherein step (b) (ii) further comprises adding a fragrance to the molten mineral oil gel.

9. The method of claim 7 wherein step (b) (ii) further comprises adding a pigment to the molten mineral oil gel.

10. The method of claim 9 wherein step (b) (ii) further comprises adding a fragrance to the molten mineral oil gel.

11. The method of claim 1 wherein step (b) comprises:

i) providing a quantity of mineral oil gel;

ii) melting the mineral oil gel;

iii) forming the molten mineral oil gel into a generally planar sheet;

iv) cooling the mineral oil gel until the sheet solidifies; and v) cutting the sheet with a die to form the component.

12. The method of claim 11 wherein step (b) (ii) further comprises adding a fragrance to the molten mineral oil gel.

13. The method of claim 11 wherein step (b) (ii) further comprises adding a pigment to the molten mineral oil gel.

14. The method of claim 13 wherein step (b) (ii) further comprises adding a fragrance to the molten mineral oil gel.

15. The method of claim 11 wherein step (b) comprises placing multiple components onto the melted top surface and step (b) (v) comprises cutting the sheet to form multiple components.

16. The method of claim 1 wherein step (b) comprises:

i) providing a quantity of mineral oil gel;

ii) melting the mineral oil gel;

iii) extruding and cooling the molten mineral oil gel through a die to form an extruded member; and iv) cutting the member to form at least one component.

17. The method of claim 16 wherein step (b) (ii) further comprises adding a fragrance to the molten mineral oil gel.

18. The method of claim 16 wherein step (b) (ii) further comprises adding a pigment to the molten mineral oil gel.

19. The method of claim 18 wherein step (b) (ii) further comprises adding a fragrance to the molten mineral oil gel.

20. A decorative candle comprising:

a container having an open end;

a quantity of wax disposed within the container and having a plurality of surfaces including a top surface disposed adjacent to the open end;

a wick disposed within the wax and protruding upwardly from the top surface; and at least one gelatinous component partially disposed within at least one of the surfaces of the wax.

21. The decorative candle of claim 20 wherein the wax comprises paraffin wax.

22. The decorative candle of claim 20 wherein the wax comprises a fragrance.

23. The decorative candle of claim 20 wherein the wax comprises a pigment.

24. The decorative candle of claim 23 wherein the wax comprises a fragrance.

25. The decorative candle of claim 20 wherein the gelatinous component is formed from a mineral oil gel.

26. The decorative candle of claim 25 wherein the mineral oil gel comprises a pigment.

27. The decorative candle of claim 25 wherein the mineral oil gel comprises a fragrance.

28. The decorative candle of claim 27 wherein the mineral oil gel comprises a pigment.

* * * * *